US00PP15084P2

(12) United States Plant Patent
Olesen et al.

(10) Patent No.: US PP15,084 P2
(45) Date of Patent: Aug. 17, 2004

(54) MINIATURE ROSE PLANT 'POULRA017'

(50) Latin Name: *Rosa hybrida*
Varietal Denomination: POULra017

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/439,997

(22) Filed: May 16, 2003

(51) Int. Cl.[7] ..... A01H 5/00
(52) U.S. Cl. ..... Plt./117
(58) Field of Search ..... Plt./117, 116, 118, Plt./124, 125

*Primary Examiner*—Anne Marie Grunberg
*Assistant Examiner*—June Hwu

(57) ABSTRACT

A new miniature rose plant which has abundant, creamy white flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULra017'.

SUMMARY OF THE INVENTION

The present discovery constitutes a new and distinct variety of a miniature pot rose plant which was discovered in a cultivated area. The mutation resulted from 'POULra002', a miniature pot rose hybridized by the same inventors. 'POULra002' is described and illustrated in U.S. Plant Pat. No. 13,275, and issued on Nov. 26, 2002. The new rose variety resulted from a naturally occurring mutation of unknown causation on a branch of 'POULra002'.

The new variety may be distinguished from its parent variety 'Poulra002' by the following combination of characteristics:

1. While flowers of the parent variety have 35 to 45 petals, 'Poulra017' has an average of 50 flower petals.
2. While the open flowers of the parent variety have a general tonality of Red Group 43C, 'Poulra017' is Yellow-Orange Group 19D.
3. While the styles, on reproductive flower parts of the parent variety are Yellow-Green Group 145B in color, 'Poulra017' is Red-Purple Group 196C.

The rose plant of the present discovery has a unique combination of characteristics which are outstanding in the new variety and which distinguish it from the original rose 'POULra002', as well as all other varieties which we are aware of. For example, the new variety has:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULra017' from all other varieties of which we are aware.

The resulting mutation was selected and evaluations were conducted on the resulting rose plants in a controlled environment. Asexual reproduction of 'POULra017' by cuttings and traditional budding was first done by L. Pernille and Mogens N. Olesen in their nursery in Fredensborg, Denmark in 1977. This initial and other subsequent propagations conducted in controlled environments have demonstrated that the characteristics of 'POULra017' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra017'. Specifically illustrated in FIG. 1:

FIG. 1.1; Stem showing branching and the attachment of leaves, buds, and peduncles;

FIG. 1.2; Flower bud, partially opened bud, and open bloom;

FIG. 1.3; Flower petals, detached;

FIG. 1.4; Sepals, receptacle, and pedicel;

FIG. 1.5; Stem as well as a bare stem exhibiting thorns;

FIG. 1.6; Leaves.

DETAILED DESCRIPTION OF THE VARIETY

The following is a description of 'POULra017', as observed in its growth in a field nursery in Jackson County, Oreg. in February of 2003. Color references are made using The Royal Horticultural Society (London, England) Colour Chart, 1995, except where common terms of color are used.

For a comparison, several physical characteristics of the rose variety 'POULra015', a rose variety from the same inventors described and illustrated in U.S. Plant Pat. No. 14,309, issued on Nov. 18, 2003 are compared to 'POULra017' in Chart 1.

CHART 1

| | 'POULra017' | 'POULra015' |
|---|---|---|
| Petalage | 50. | 13 to 15. |
| General tonality | Yellow-Orange Group 19D. | Yellow Group 11D. |
| Thorn incidence | 6 thorns per 10 cm of stem. | 0 thorns per 10 cm of stem. |

Parents: Sport of 'POULra002'.
Classification:
*Botanical.*—*Rosa hybrida* POULra017.
*Commercial.*—Miniature.

FLOWER AND FLOWER BUD

Blooming habit: Recurrent.
Flower bud:
*Size.*—Upon opening, 25 mm in length from base of receptacle to end of bud. Bud diameter is 10 mm on average.
*Bud form.*—Short, pointed ovoid.
*Bud color.*—As sepals unfold, Yellow-Orange Group 19D; Yellow-Orange Group 19D at ¼ opening.
*Sepals.*—Margins are Yellow-Green Group 144A; interior is Yellow-Green Group 144B. Weak foliaceous appendages on three of the five sepals. Upper surfaces of sepals are moderately pubescent. Stipitate glands are present on sepal edges. Shape: Sepal apex is cirrose. Base is flat at union with receptacle. Size: 21 mm long×6 mm wide.
*Receptacle.*—Surface: Smooth. Shape: Funnel-shaped. Size: 8 mm (h)×5 mm (w). Color: Yellow-Green Group 144A.
*Peduncle.*—Surface: With scant stipitate glands. Length: 25 to 28 mm average length. Color: Yellow-Green Group 144A. On plants grown under high light conditions, peduncle may exhibit intonations of Greyed-Red Group 181A. Strength: Strong.
*Borne.*—Clusters of 2 to 3 blooms.
*Anthocyanin.*—Greyed-Red Group 181A, when present.
Flower bloom:
*Fragrance.*—Light.
*Duration.*—As a pot plant, flowers last from 10 to 14 days.
*Size.*—Medium for a 8–11 cm pot rose. Average flower diameter is 40 mm when open.
*Form.*—Shape of flower when viewed from the side: Upon opening, upper part: Flattened convex. Upon opening, lower part: Convex. Open flower, upper part: Flattened convex. Open flower, lower part: Flat.
*Petalage.*—Average range: 50 petals under normal conditions with 4 to 6 petaloids.
Color:
*Upon opening, petals.*—Outermost petals: Outer Side: Blend of Yellow-Orange Group 19D and Green White Group 157A. Inner Side: Blend of Yellow-Orange Group 19D and Green White Group 157A. Innermost petals: Outer Side: Yellow-Orange Group 19D. Inner Side: Yellow-Orange Group 19D.
*Upon opening, basal petal spots.*—Outermost petals: Outer Side: Green-Yellow Group 1C. Inner Side: Green-Yellow Group 1C. Innermost petals: Outer Side: Green-Yellow Group 1C. Inner Side: Green-Yellow Group 1C.
*After opening, petals.*—Outermost petals: Outer Side: Blend of Yellow-Orange Group 19D Yellow-White Group 158D and Green White Group 157A. Outer surfaces also exhibit intonations of Yellow-Green Group 145C. Inner Side: Blend of Yellow-Orange Group 19D and Green White Group 157A. Innermost petals: Outer Side: Yellow-Orange Group 19D. Inner Side: Yellow-Orange Group 19D.
*After opening, basal petal spots.*—Outermost petals: Outer Side: Green-Yellow Group 1C. Inner Side: Green-Yellow Group 1C. Innermost petals: Outer Side: Green-Yellow Group 1C. Inner Side: Green-Yellow Group 1C.
General tonality: On open flower, Yellow-Orange Group 19D with intonations of Yellow-Orange Group 19B to 19C. No change in the general tonality at the end of the 10th day. Afterwards, general tonality is Yellow-Orange Group 19D.
Petals:
*Petal reflex.*—Slight.
*Petal edge.*—Ruffled.
*Shape.*—Base is rounded, apex is broadly rounded.
*Size.*—20 mm (l)×22 mm (w).
*Petaloids.*—Quantity: 4 to 6. Size: 8 mm (l)×5 mm (w). Color: Yellow-Orange Group 19D.
*Thickness.*—Average.
*Surface texture.*—Smooth.
*Arrangement.*—Formal.
Reproductive organs:
*Pollen.*—Color: Yellow-Orange Group 17C. Quantity: Scant.
*Anthers.*—Size: 2 mm long. Color: Greyed-Orange Group 177A. Quantity: 55.
*Filaments.*—Color: Yellow Group 2B. Length: 3 to 4 mm.
*Pistils.*—Quantity: 47.
*Stigmas.*—Slightly inferior in location to anthers. Color: Greyed-Green Group 196C.
*Styles.*—Color: Red-Purple Group 196C. Length: 2 to 3 mm.
*Seed formation.*—No hips observed.

PLANT

Plant growth: Vigorous, compact, upright to bushy. When grown as a 8–11 cm pot plant, the average height of the plant itself is 20 to 25 cm and the average width is 25 cm.
Stems:
*Color.*—Young wood: Yellow-Green Group 144B. Older wood: Yellow-Green Group 144A.
*Prickles.*—Incidence: 6 thorns per 10 cm of stem. Size: Average length: 4 mm. Color: Greyed-Yellow Group 160D, with intonations of Greyed-Red Group 181B. Shape: Linear.
*Surface.*—Young wood: Smooth. Older wood: Smooth.
Plant foliage: Normal number of leaflets on normal leaves in middle of the stem: 5 leaflets.
*Leaf size.*—75–100 mm (l)×45–50 mm (w).
*Quantity.*—Average.
*Color.*—Mature foliage: Upper Leaf Surface: Green Group 137A. Lower Leaf Surface: Greyed-Green Group 191B. Juvenile foliage: Green Group. Upper Leaf Surface: Green Group 137A. Lower Leaf Surface: Green Group 138B. Anthocyanin intonation: Location: On plants grown under high light conditions, leaf margins, developing leaves, peduncle, and stems may exhibit intonations of Greyed-Red Group 181A.
Plant leaves and leaflets:
*Stipules.*—Size: 8 mm in length. Color: Yellow-Green Group 144B. Presence of stipitate glands: On stipule edges. Anthocyanin: Greyed-Red Group 181A.
*Petiole.*—Length: 20 mm. Color: Yellow-Green Group 144B. Underneath: Yellow-Green Group 144B. Margins: Greyed-Red Group 181A. Anthocyanin:

Greyed-Red Group 181A. Surface Texture: Somewhat rough. Shallow prickles observed on underside of petiole.

*Rachis.*—Color: Yellow-Green Group 144B. Underneath: Yellow-Green Group 144B. Margins: Greyed-Red Group 181A. Anthocyanin: Greyed-Red Group 181A. Surface Texture: Somewhat Rough. Shallow prickles observed on undersides of the rachis, with 1 to 2 thorns.

*Leaflet.*—Edge: Finely serrated. Shape: Ovate. The base is rounded. Apex shape is acute. Thickness: Thin. Glossiness: Glossy. Arrangement: Odd pinnate. Venation: Reticulate.

Disease resistance: Average resistance to mildew, black spot, and Botrytis under normal growing conditions in a glasshouse in Burlington, Canada.

What is claimed is:

1. A new and distinct variety of rose plant of the miniature class, substantially as herein illustrated and described as a distinct and novel rose variety due to its abundant, creamy white flowers, vigorous growth, compact habit, suitability for production from softwood cuttings in pots, and durable flowers and foliage which make the variety suitable for distribution in the floral industry.

* * * * *

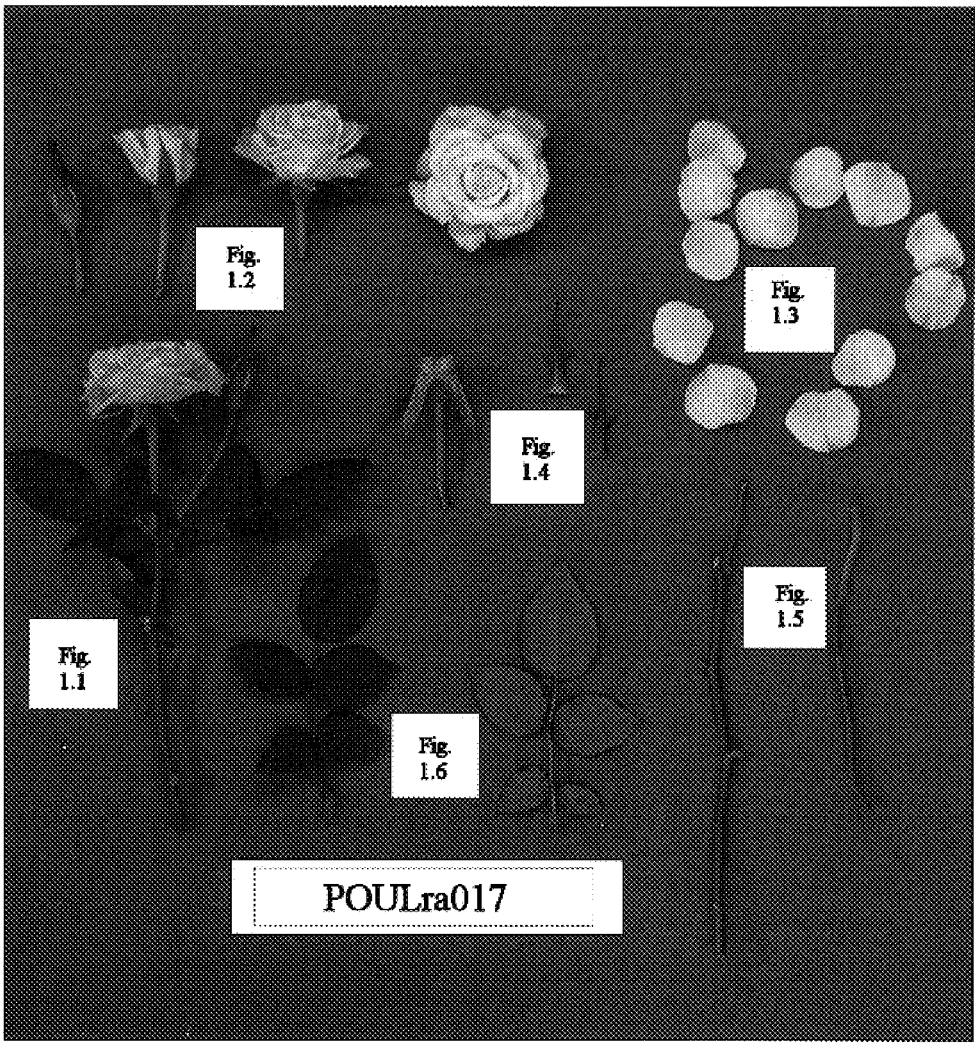
Fig. 1.2
Fig. 1.3
Fig. 1.4
Fig. 1.5
Fig. 1.1
Fig. 1.6
POULra017